(12) United States Patent
Balu et al.

(10) Patent No.: US 10,595,770 B2
(45) Date of Patent: Mar. 24, 2020

(54) IMAGING PLATFORM BASED ON NONLINEAR OPTICAL MICROSCOPY FOR RAPID SCANNING LARGE AREAS OF TISSUE

(71) Applicant: The Regents of the University of California, Oakland, CA (US)

(72) Inventors: Mihaela Balu, Irvine, CA (US); Eric O. Potma, Irvine, CA (US); Bruce J. Tromberg, Irvine, CA (US); Hideharu Mikami, Tokyo (JP)

(73) Assignee: The Regents of the University of California, Oakland, CA (US)

( * ) Notice: Subject to any disclaimer, the term of this patent is extended or adjusted under 35 U.S.C. 154(b) by 298 days.

(21) Appl. No.: 15/786,485

(22) Filed: Oct. 17, 2017

(65) Prior Publication Data
US 2018/0106729 A1 Apr. 19, 2018

Related U.S. Application Data

(60) Provisional application No. 62/410,152, filed on Oct. 19, 2016.

(51) Int. Cl.
*A61B 5/00* (2006.01)
*G01N 21/64* (2006.01)
(Continued)

(52) U.S. Cl.
CPC ............ *A61B 5/444* (2013.01); *A61B 5/0064* (2013.01); *A61B 5/0071* (2013.01);
(Continued)

(58) Field of Classification Search
CPC .. G01N 21/8851; G01N 21/6458; A61B 5/40; A61B 5/0082; A61B 2562/0233;
(Continued)

(56) References Cited

U.S. PATENT DOCUMENTS 5,034,613 A * 7/1991 Denk ................. G01N 21/6402
250/458.1
5,532,873 A * 7/1996 Dixon ................ G02B 21/0044
359/368

(Continued)

*Primary Examiner* — Que Tan Le
*Assistant Examiner* — Jennifer D Bennett
(74) *Attorney, Agent, or Firm* — Marcus C. Dawes; Daniel L. Dawes

(57) ABSTRACT

A multiphoton microscope based on two-photon excited fluorescence and second-harmonic generation that images FOVs of about 0.8 mm² (without stitching adjacent FOVs) at speeds of 10 frames/second (800×800 pixels) with lateral and axial resolutions of 0.5 μm and 2.5 μm, respectively. The scan head of the instrument includes a fast galvanometric scanner, relay optics, a beam expander and a high NA objective lens. The system is based on a 25×, 1.05 NA water immersion lens, which features a long working distance of 1 mm. A proper tailoring of the beam expander, which consists of the scan and tube lens elements, enables scaling of the FOV. The system and method also include a flat wavefront of the beam, minimum field curvature, and suppressed spherical aberrations. All aberrations in focus are below the Marechal criterion of 0.07λ rms for diffraction-limited performance.

24 Claims, 6 Drawing Sheets
(1 of 6 Drawing Sheet(s) Filed in Color)

(51) Int. Cl.
*G02B 21/00* (2006.01)
*G02B 27/58* (2006.01)
*G01N 21/88* (2006.01)

(52) U.S. Cl.
CPC ....... *A61B 5/0082* (2013.01); *G01N 21/6458* (2013.01); *G01N 21/8851* (2013.01); *G02B 21/0048* (2013.01); *G02B 21/0072* (2013.01); *G02B 21/0076* (2013.01); *G02B 27/58* (2013.01); *A61B 2562/0233* (2013.01); *G02B 2207/114* (2013.01)

(58) Field of Classification Search
CPC ..... A61B 5/444; A61B 5/0071; A61B 5/0064; G02B 21/00; G02B 21/0076; G02B 21/0072; G02B 21/0048; G02B 27/58; G02B 2207/114
See application file for complete search history.

(56) References Cited

U.S. PATENT DOCUMENTS

| | | | | |
|---|---|---|---|---|
| 6,356,088 | B1* | 3/2002 | Simon | G02B 21/002 324/762.01 |
| 8,696,122 | B2* | 4/2014 | Hammer | A61B 3/102 351/205 |
| 2013/0211391 | A1* | 8/2013 | BenYakar | A61B 18/20 606/10 |
| 2018/0292321 | A1* | 10/2018 | Fiolka | G01N 21/6458 |

* cited by examiner

IMAGING PLATFORM BASED ON NONLINEAR OPTICAL MICROSCOPY FOR RAPID SCANNING LARGE AREAS OF TISSUE

RELATED APPLICATIONS

The present application is related to U.S. provisional patent application Ser. No. 64/410,152, filed on Oct. 19, 2016, which is incorporated herein by reference and to which priority is claimed pursuant to 35 USC 119.

GOVERNMENT SUPPORT

This invention was made with Government support under Grant No. EB015890, awarded by the National Institutes of Health. The Government has certain rights in this invention.

BACKGROUND

Field of the Technology

The invention relates to the field of laser-scanning based nonlinear optical microscope for rapid imaging of wide areas and large volumes of biological tissues or other materials, ex vivo or in vivo, at sub-micron resolution. Applications include but are not limited to clinical skin imaging, non-invasive skin cancer diagnosis.

Description of the Prior Art

In vivo multiphoton microscopy (MPM) is emerging as an important research and clinical tool for label-free imaging in human skin. The clinical applications of in vivo label-free MPM span from skin cancer detection and diagnosis, to characterizing and understanding keratinocyte metabolism, skin aging, pigment biology, and cosmetic treatments. MPM is based on laser-scanning microscopy, a technique that utilizes a focused laser beam that is raster-scanned across the sample to create high-resolution images. A three dimensional view of the skin can be reconstructed by scanning at multiple depths. Importantly, high-resolution imaging is combined with a label-free contrast mechanism. MPM contrast in skin is derived from second harmonic generation (SHG) of collagen and two-photon excited fluorescence (TPEF) of tissue components such as the co-factors NADH and FAD+, elastin, keratin, and melanin.

Clinical examination crucially relies on the ability to quickly examine large tissue areas and rapidly zoom in to regions of interest. Skin lesions often show irregularity in color and appearance, especially when they start to progress towards malignancy. Imaging of large field of views (FOVs) and automatic translation of the imaging area are critical in the assessment of the entire lesion to avoid false negative diagnosis. Commercial clinical microscopes based on MPM and reflectance confocal microscopy (RCM) have implemented automatic translation of the imaging area. However, the initial FOV is limited to or less than $0.5 \times 0.5$ mm$^2$ and thus, assessing large areas of tens of mm$^2$ at different depths may be time consuming and not feasible for clinical use. In an ideal system large FOV and automatic translation of the imaging area would be complemented by fast image acquisition and high detection sensitivity in order for such a system to be of practical utility and efficient use for fast full assessment of skin lesions.

Nonlinear optical (NLO) microscopy comprises a set of imaging techniques that provide high three dimensional resolution and label-free molecular contrast of endogenous components in specimens. NLO microscopy utilizes a focused laser beam that is raster-scanned across the sample to create high-resolution images upon signal detection. A three dimensional-view of the sample can be reconstructed by scanning at multiple depths. Biological tissues are of particular interest owing to NLO microscopy attributes that are tailored for their noninvasive visualization. The list of addressable tissue components includes collagen (through second harmonic generation, SHG), flavin adenosine dinucleotide (FAD), reduced nicotinamide adenine dinucleotide (NADH), keratin, melanin, and elastin fibers (through two-photon excited fluorescence, TPEF), lipids, proteins and water (through coherent Raman scattering, CRS). Endogenous components in biological tissues can also be visualized through third harmonic generation (THG) contrast derived from refractive index discontinuities at interfaces. While this technique does not feature specific molecular contrast, it can be a valuable tool when combined with other imaging modalities, as its higher order nonlinearity and long excitation wavelength provide improved three dimensional-resolution and penetration depth.

The ability to generate high resolution maps of specific tissue molecular compounds without the need for extrinsic labels sets NLO imaging techniques apart from other biomedical imaging methods, and classifies these techniques as preferred tools for label-free imaging of superficial tissues in vivo.

Because of its near-ideal attributes for imaging superficial tissues, NLO microscopy has attracted attention as a high-resolution visualization method of skin in vivo. Koenig et. al. "Flexible Nonlinear Laser Scanning Microscope for Noninvasive Three-Dimensional Detection," U.S. Pat. No. 9,176,309, discloses a system design for flexible, non-invasive, three-dimensional laser-scanning microscopy using SHG, CARS and multiphoton fluorescence signals such as TPEF from living and non-living matter. A clinical microscope based on this disclosed design has been used in several clinical applications such as skin cancer detection and keratinocyte metabolism assessment. The design includes a scanning unit for two-dimensional deflection of the laser beams, and an image recording based on time-correlated single photon counting (TCSPC).

The disadvantages of the prior design are twofold: 1) The TCSPC detection method is associated with relatively long pixel dwell times (~20 µs), limiting the scanning speed to a maximum of few seconds per/frame for 512×512 pixels/frame. This detection strategy is not compatible with faster scanning rates that are desirable in many clinical settings; and 2) the close proximity of the mirrors in the scanning unit introduces a motion of the beam at the entrance pupil of the focusing optics that limits the field of view. These shortcomings limit the scanning speed and field of view (FOV). Limited scanning area and slow speed are major limitations for diagnosis and treatment monitoring clinical applications with current technology. Both of those limitations are overcome by the disclosed embodiments of the invention, resulting in a major increase of clinical applicability. Maximizing scanning speed and FOV cannot be achieved in a straightforward manner in the prior art design due to its optical and detection designs as described above.

Advances in the development of NLOM-based microscopes that can image large FOVs have been recently made by several research groups. Prior endeavors have reported on developing an NLOM-based system that can image up to 80 mm$^2$ at a maximum speed of 5 mm/ms by trading-off lateral resolution (between 1.2 µm and 2 µm across the entire FOV). This microscope was applied for imaging resting-state vasomotion across both hemispheres of a murine brain through a transcranial window without the need to stitch adjacent imaging areas. In-depth optimization studies of scan and tube lens designs for minimizing optical aberrations associated with large angle scanning using conventional galvanometer scanning have been produced. Higher scan speeds provided by resonant scanner as the fast axis and conventional galvanometer as the slow axis have been previously implemented in MPM-based systems for several applications, including skin imaging. Neither of prior designs includes all required features for an efficient clinical microscopy imaging device: fast scanning, large FOV, sub-micron resolution.

What is needed therefore for efficient clinical microscopy imaging is an MPM imaging method and apparatus which can image rapidly (<1 μs pixel dwell time), large areas (at least 800×800 μm$^2$) without compromising resolution (sub-micron).

BRIEF SUMMARY

The illustrated embodiments of the invention provide an imaging platform based on laser-scanning nonlinear optical microscopy that can scan rapidly (<1 μs pixel dwell time) large areas (at least 800×800 μm$^2$) while maintaining a sub-micron resolution. The images are generated through the detection of NLO signals from the interaction of the laser light with matter (e.g. tissue). The instrument can be used ex vivo or in vivo, in biological tissues or other materials that provide either endogenous or exogenous molecular contrast.

An NLO clinical platform including the aforementioned features can broadly impact practical clinical imaging in general and skin imaging in particular, as a tool for: 1) in vivo, non-invasive skin assessment to help medical practitioners improve their clinical diagnosis of early stage (skin) diseases when the uncertainty of their decision is likely to be higher than in the case of advanced disease. Diagnosis of borderline cases and early stage of melanoma represents a particular interest. Accurate non-invasive diagnosis would reduce the number of biopsies, cost and pain. 2) in vivo, non-invasive monitoring of skin treatments; 3) ex vivo assessment of skin excisions where, besides lateral margins, tumor invasion needs to be evaluated (samples can be imaged from both top and bottom sides). This is particularly important in more advanced cases of diseases, such as skin cancer and in Mohs surgeries (progressive removal and examination of cancer-containing skin layers until only cancer-free tissue remains). This would reduce time for diagnosis, clinical procedures and cost.

The disclosed embodiments of the invention differs from the prior art by allowing for much larger FOV while at the same time increasing the scan speed without compromising resolution. The embodiment is illustrated in an imaging platform based on laser-scanning microscopy that can scan rapidly large areas while maintaining a sub-micron resolution.

The instrument we describe cumulates well-known components in a design for rapid scanning of large volumes of biological tissues with wide-area scanning, three dimensional imaging in scattering media, and sub-micron resolution. Our embodiments of the invention overcome two main disadvantages related to conventional microscopes based on laser-scanning microscopy: 1) limited scanning area (field of view), and 2) slow acquisition rates of large areas The microscope we describe can scan wider areas than standard microscopes (at least 5× improvement) and faster than conventional scanning-based microscopes (at least 15× improvement). Importantly, these improvements are achieved without compromising the sub-micron resolution.

The illustrated embodiments of the invention include an apparatus for performing nonlinear optical laser microscopy in a clinical setting. The apparatus includes: a pulsed laser to produce a laser beam; an imaging head optically coupled to the pulsed laser for scanning tissue with a predetermined size of a field of view with submicron resolution at a predetermined rate; and an image and data acquisition system associated with the imaging head to acquire and process submicron optical data in the predetermined size of the field of view at the predetermined rate.

The imaging head includes: a resonant scanning mirror optically coupled to the pulsed laser; a relay lens system optically coupled to the resonant scanning mirror a galvo mirror optically coupled to the relay lens system; a beam expander optically coupled to the galvo mirror, and a microscope objective optically coupled to the beam expander, the microscope objective for scanning the tissue and returning a nonlinear optical signal from the tissue to the detectors and data acquisition system.

In a preferred embodiment the light is provided by one or more than one ultrafast laser systems (lasers with pulse durations of femtoseconds or picoseconds).

The resonant scanning mirror operates at at least a 4 kHz scan frequency to steer the beam in the x direction and where the galvo mirror steers the laser beam in the y direction.

The microscope objective provides submicron resolution by being a high numerical aperture (NA)-low magnification combination microscope objective.

The beam has a large diameter and the relay lens system and beam expander are designed to compensate for the optical aberrations introduced by the large beam diameter and scanning angles and to overfill the back aperture of the microscope objective.

In one example, the relay lens system can include four achromat lenses forming a 1:1 relay lens imaging system with an RMS wavefront error at 800 nm of 0.06, providing diffraction-limited performance for more than ⅔ of the FOV.

In one example, the beam expander can include four doublet achromatic lenses with an RMS wavefront error at 800 nm of 0.07, providing diffraction-limited performance for more than ⅔ of the FOV.

In one embodiment the relay lens system and beam expander each have an optical axis and the optical axes of the relay lens system and beam expander are configured at right angles to each other as coupled through the galvo mirror.

In another embodiment a folding mirror in included and the relay lens system and beam expander each have an optical axis and the optical axes of the relay lens system and beam expander are folded parallel to each other as coupled through the folding mirror and the galvo mirror to provide a compact optical layout.

The scope of the illustrated embodiments of the invention also includes a method for scanning tissue with a predetermined size of a field of view with submicron resolution at a predetermined rate. The method includes the steps of: generating a pulsed laser beam; scanning the pulsed laser beam with a resonant scanning mirror; coupling the scanned pulsed laser beam from the resonant scanning mirror to a relay lens system optically coupled to the resonant scanning mirror scanning the pulsed laser light from the relay lens system with a galvo scanning mirror; coupling the scanned pulsed laser beam from the galvo scanning mirror to a beam expander; overfilling a back aperture of a microscope objective optically coupled to the beam expander; and returning the nonlinear optical signals from the tissue to detectors and data acquisition system.

The method may include the step of providing the laser source either inside the imaging head or exterior to the imaging head.

The step of scanning the pulsed laser beam includes the step of scanning the pulsed laser beam with the resonant scanning mirror at at least a 4 kHz scan frequency in the x direction and scanning the laser beam in the orthogonal y direction with the galvo scanning mirror.

The method further includes the step of providing the microscope objective with a high numerical aperture (NA)-low magnification combination to achieve the submicron resolution.

The method further comprises providing a relay lens system and beam expander arranged and configured to compensate for the optical aberrations introduced by the large beam diameter and scanning angles and to overfill the back aperture of the microscope objective.

The step of providing the relay lens system includes the step of providing four achromat lenses forming a 1:1 relay lens imaging system with an RMS wavefront error at 800 nm of 0.06 and more than ⅔ of the FOV being diffraction-limited.

In one embodiment the step of providing the beam expander includes the step of providing four doublet achromatic lenses with an RMS wavefront error at 800 nm of 0.07 and more than ⅔ of the FOV being diffraction limited.

In another embodiment the method may further comprise the step of providing a simple beam expander between the laser and the resonant scanning mirror to provide a pulsed beam of enlarged diameter.

Invention specifically includes an apparatus for performing nonlinear optical laser microscopy of tissue or other material at fast rate (less than 1 μs pixel dwell time), on a large area (at least 800×800 μm$^2$) and at sub-micron resolution. The apparatus includes: one or more than one sources of pulsed laser light beam(s); a resonant scanning mirror optically coupled to the laser source(s) of laser light beam(s) for scanning the laser light beam(s) in the x direction; a relay lens system optically coupled to the resonant scanning mirror to avoid vignetting and reduction of a field of view of the pulsed laser light beam(s) when scanned; a galvanometer scanning mirror optically coupled to the relay lens system for scanning the pulsed laser light beam(s) in the y direction; a beam expander optically coupled to the galvanometer scanning mirror; and a high numeric aperture, low power microscope objective optically coupled to the beam expander, the microscope objective having a back aperture which is overfilled by the beam expander to achieve submicron resolution of scanned tissue and returning a nonlinear optical signal from the scanned tissue to at least two detectors such as photomultiplier tubes (PMTs) couple to the image and data acquisition system.

The apparatus further includes an image and data acquisition system to acquire and process submicron optical data in a predetermined clinical size of a field of view at the predetermined clinical scanning rate.

In one embodiment the source of pulsed laser light beam, the resonant scanning mirror, the relay lens system, the galvanometer scanning mirror, the beam expander, the high numeric aperture low power microscope objective and the detectors are combined in a single imaging head as a compact integrated optical system.

In another embodiment the resonant scanning mirror, the relay lens system, the galvanometer scanning mirror, the beam expander, the high numeric aperture low power microscope objective and detectors are combined in a single imaging head, and the source of pulsed laser light beam is exterior to the imaging head and coupled thereto by the optical arm.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

The feedback provided by the clinical studies involving a conventional prior art microscope reveals that such a design lacks the potential to provide non-invasive diagnosis. In order for a clinical microscope to be efficiently used for disease diagnosis and treatment guiding, namely for clinical-decision making at the bedside, four requirements are necessary:

1. Sub-micron resolution for identifying cellular and sub-cellular features in a similar manner with histopathology, the gold-standard diagnosis method.
2. Large FOV assessment. Lesions often show irregularity in color and appearance in general, especially when they start to progress towards malignancy. Imaging of limited FOV of the lesion can easily result in false negative diagnosis.
3. Fast scanning speed. Long acquisition times introduce motional artifacts in the images and also negatively affect the patient recruitment process.
4. Reduced barriers-to-access and cost effectiveness, such as reduced complexity of design, reduced cost, enhanced compactness and enhanced portability.

Prior art designs fulfills requirement (1). Requirements (2)-(4) cannot be implemented together in a straightforward manner with conventionally available designs.

Basic Layout of the Imaging Platform

Figure 1:
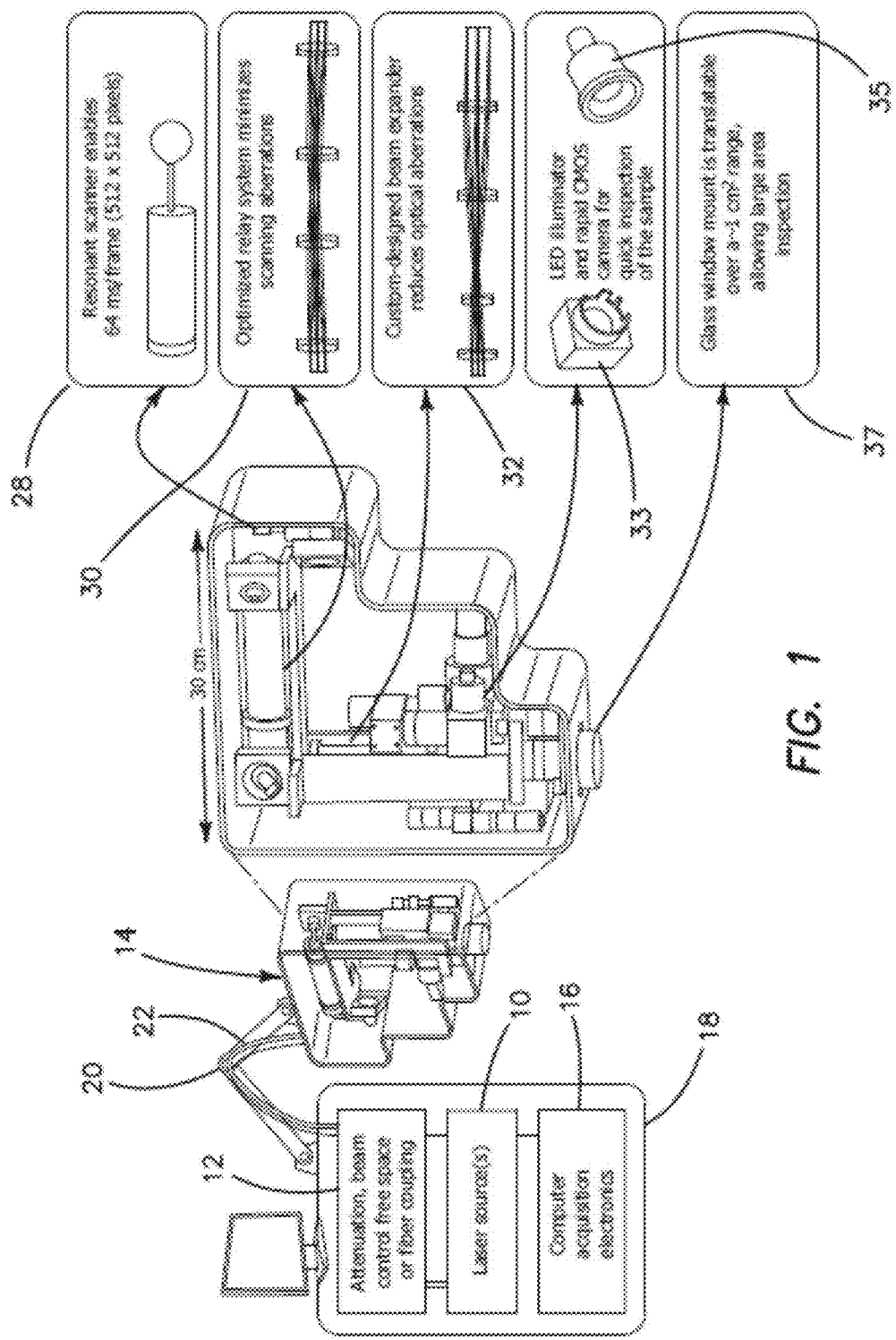
FIG. 1 is a conceptual schematic of the basic layout of the proposed clinical microscope. The schematic is not to scale.

In one embodiment, the system as shown in FIG. 1 is comprised of three main parts: one or more ultrafast laser 10 (lasers with pulse durations of femtoseconds or picoseconds) outside the imaging head 14, a beam control box 12 and an imaging head 14. The laser 10, beam control box 12 and computer 16 are placed on a cart 18. The imaging head 14 is mounted with a flexible mechanical arm 20 to the cart 18. The laser light is coupled to the imaging head 14 through an optical fiber or an articulated optical arm 22. This design fulfills requirements (1)-(3) described above and it has the benefit of wavelength tunability as commonly provided by Ti:Sapphire lasers since such a laser can be housed on the cart.

Figure 6:
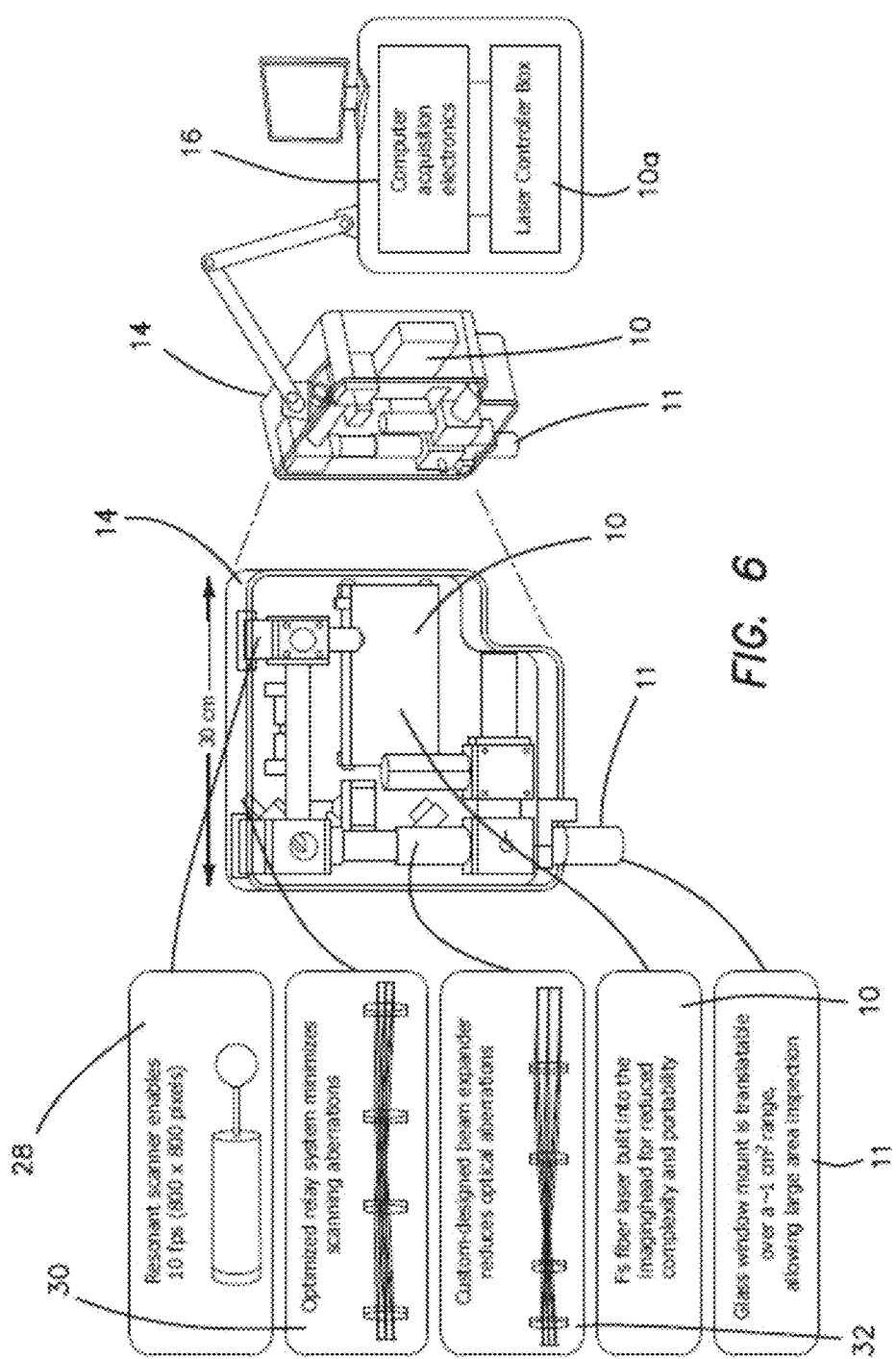
FIG. 6 is a schematic diagram of another embodiment of the system shown in the left side of the figure in an opened plan view of the imaging head and in the right side as a perspective semi-transparent view of the entire system, where the laser is included within the imaging head.

In another embodiment, in the system as shown in FIG. 6 one or more than one laser 10 (femtosecond or picosecond) is built-into the imaging head 14. The laser 10 needs to have a compact design such as a dual-wavelength fiber laser. A laser controller box 10a is provided exterior to imaging head 14 with computer acquisition electronics 16 as in the embodiment of FIG. 1. The embodiment of FIG. 6 also includes a glass window mount 11 which is translatable over a range of approximately 1 $cm^2$ to allow large area inspection. The laser control box 10a and computer 16 are placed on cart. The imaging head 14 is mounted with a flexible mechanical arm to the cart. There is no need for an additional optical arm for coupling the light in the imaging head 14. This design is particularly unique as it meets all the requirements (1)-(4) for the instrument to be efficiently used for clinical-decision making as the patient bedside. It also provides enhanced compactness, portability as well as reduced cost and complexity at the expense of wavelength tunability.

For either of the two embodiments, the imaging head 14 can be used for generation and detection of any nonlinear optical signals such as TPEF, SHG, THG and CRS. TPEF signal can be generated by endogenous fluorophores in tissues or other materials or by exogenous fluorophores (labeling).

For either of the two embodiments, an LED or another illumination source 33, along with a CMOS or a CCD camera 35 can be implemented for quick inspection of the sample. Bright field illumination, a critical feature for retrieving areas pre-identified by dermatologists, is currently absent in clinical NLO microscopy. The microscope is equipped with a glass imaging window 37 to enable the mesoscale imaging. The glass window 37 is mounted on a servo-controlled miniature translation stage with an extendable range of ~1 cm along both lateral coordinates. Because the glass window 37 is fixed to the skin with a light adhesive, and the skin is highly elastic, movement of the window 37 will result in lateral displacement of the superficial tissue layers. This constitutes a safe and simple way for lateral scanning without physically displacing the scan head 14 itself. The lateral position of the window 37 is controllable through the software and can be dynamically adjusted while capturing images.

Requirements (1)-(3) will be implemented by means of three components (for sub-micron resolution, high speed and enhanced FOV) included in the imaging head 14 for both embodiments described above. Thus, the sub-micron resolution is achieved by a high numerical aperture (NA)-low magnification combination microscope objective 34 (component 1). Objective 34 in conjunction with a specific optical design and location of the scan and tube lenses provide enhanced FOV (component 2). The scan rate is increased by implementing a resonant scanning mirror 24 with at least 4 kHz scan frequency (component 3) for scanning the laser beam in the x direction, and a galvanometer scanning mirror 26 for scanning the laser beam in the orthogonal y direction. Although other scanning mechanisms exist, a resonant-galvanometer scanner combination is preferable for this design purpose due to its reduced size and flexibility that it provides in selecting the frame size.

Figure 2A:
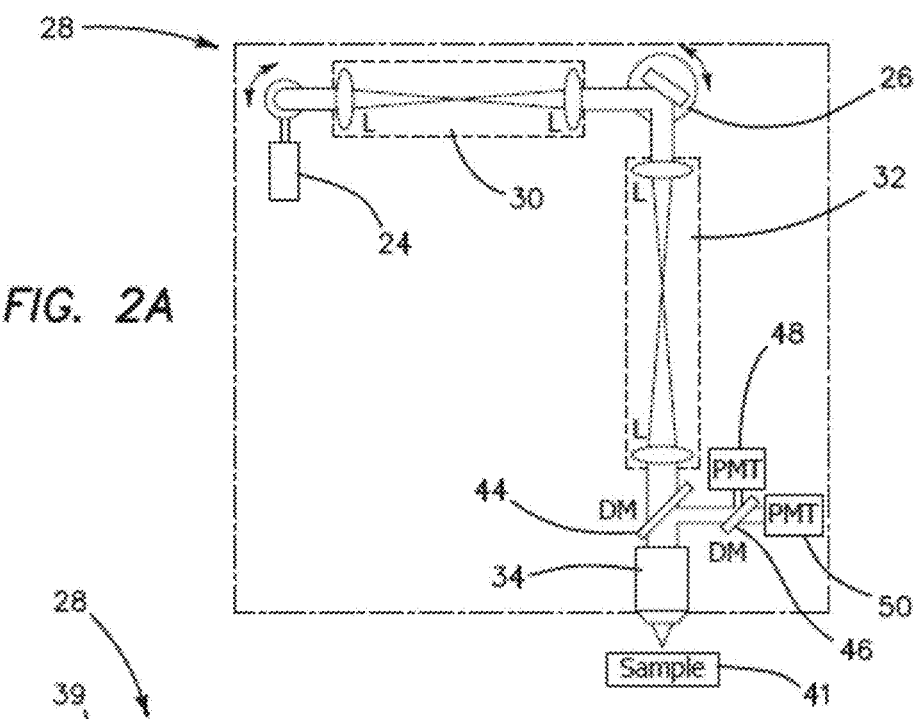
FIG. 2A is a schematic of the imaging head implemented in the current microscope, where L denotes a lens or system of lenses; M denotes a mirror; DM denotes a dichroic mirror; and PMT denotes a photomultiplier tube.
Figure 2B:
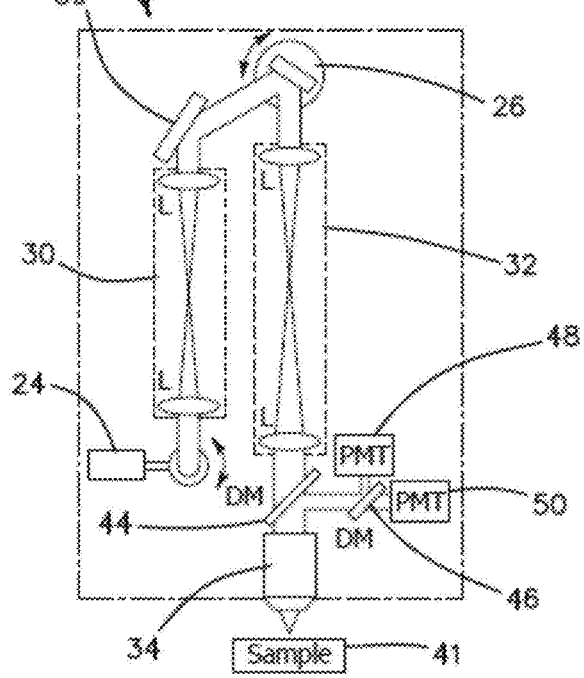
FIG. 2B is a schematic of an alternative embodiment of the imaging head implemented in the current microscope.
Figure 4A:
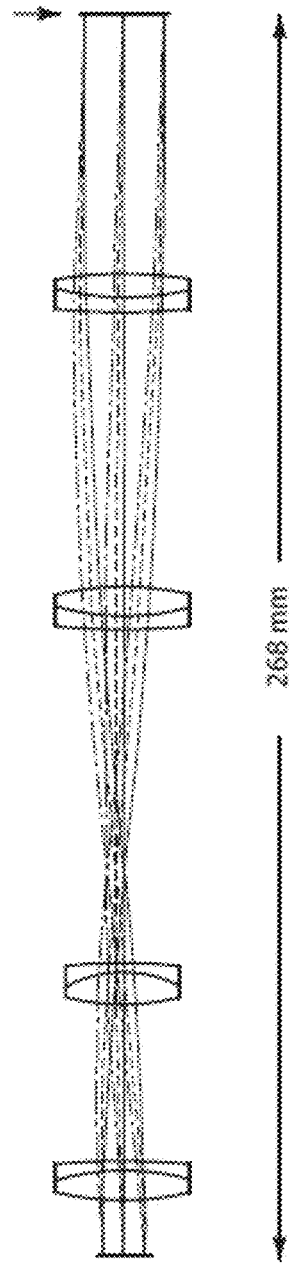
FIG. 4A is a schematic of an optical layout of the beam expander with the vertical line indicating the surface at which the aberrations are reported.

A first embodiment, the design of FIG. 2A, has the benefit of wavelength tunability as commonly provided by Ti:Sapphire laser(s) 10 since such a laser can be housed on the cart 18. A second embodiment, the design of FIG. 2B provides enhanced compactness by folding the optical path within imaging head 14 using a folding mirror 39, portability as well as reduced cost and complexity at the expense of wavelength tunability since this design requires a compact fiber based laser that usually runs at one or two wavelengths.

Implementation of Fast Imaging Acquisition

The illustrated embodiment includes a resonant scanning mirror 24 with at least 4 kHz scan frequency, and a galvanometer scanning mirror 26 for scanning the laser beam in the x and y directions. A 4 kHz resonant scanner 24 enables 64 ms/frame for a frame of 512×512 pixels, a standard pixel size in laser scanning microscopy. If such a frame covers a 1 $mm^2$ field of view, a 1 $cm^2$ area can be scanned in approximately 6.4 seconds through stitching (automatic imaging and stitching of adjacent field of views), a procedure commonly used in laser scanning microscopy. In order to visualize the three dimensional morphology of the lesions, z-stacks of images (optical sections) are acquired at different depths. As a 1 $cm^2$ area of tissue can be scanned in 6.4 seconds, a stack of 100 images of 1 cm² area acquired with a 5 μm step (0.5 mm total depth of the tissue) would take about 10 minutes to acquire. A 4 kHz resonant scanner 24 that enables 64 ms/frame (512×512 pixels) results in 0.24 μs pixel dwell time, a 15 times improvement in scanning speed comparing to a maximum of 3.8 μs pixel dwell time obtained with conventional galvanometer scanners.

Implementation of a Wide Field of View (FOV)

In a laser-scanning microscope, the FOV is determined by the objective focal length ($f_{obj}$) and the scanning angle at the back aperture of the objective ($\phi$):

$$FOV = 2 \times f_{obj} \times \tan \phi, \qquad (1)$$

where $\phi$ is measured from the optical axis and thus, it is half of the full scanning angle. A large FOV is achieved for long objective focal lengths and large scanning angles. Both of these parameters result in limited spatial resolution, as long focal lengths correspond to low magnification and low numerical aperture (NA) objectives, while large scanning angles lead to optical aberrations such as coma and astigmatism. Once the focal length is determined based on the selection of the objective, the FOV is limited by the scanning angle. The scanning angle of the mirrors depends on the magnification of the system. Low magnification is required to minimize the scanning angle and optical aberrations such as comatic aberration and astigmatism. The objective entrance pupil diameter determines the beam size before objective. The laser beam can be adjusted to over or under fill the back aperture of the objective in order to achieve spatial resolution and signal quality at depth in the tissue, as allowed by the objective NA. This task is performed by a beam expander, which consists of scan and tube lens elements.

A common limitation of the FOV in conventional laser-scanning microscopes, where the scanning mirrors are placed in proximity, is related to the motion of the laser beam at the back aperture of the objective. This is due to the beam displacement by the first mirror 24 on the second mirror 26, which for large angles, can lead to vignetting and reduction of the FOV. A relay lens system 30 between the scanning mirrors 24 and 26 addresses this limitation.

The relay and beam expander optical systems need to be chosen and designed in order to compensate for the optical aberrations introduced by the large beam diameter and scanning angles. Simulation and optimization of the imaging systems can be carried out using a computer-aided design software such as ZEMAX (Radiant ZEMAX LLC).

The MPM system 28 shown in FIGS. 2A and 2B includes a fast resonant scanning mirror 24, a galvanometric scanner 26, relay lens system 30, a beam expander 32 and a high NA objective lens 34. The selection of the objective 34 determines the main optical design considerations of the microscope. We have designed the prototype system based on the 25×, 1.05 NA water immersion lens from Olympus (XLPL25XWMP), one of the premier tissue imaging objectives that features a long working distance of 2 mm. This objective 34 has a focal distance of 9.6 mm (assuming a tube lens focal length of 180 mm used by Olympus) and an entrance pupil diameter of approximately 15 mm. We describe below in detail the main components of the system.

Our prototype design is based on a resonant scanner 24 (Cambridge Technology), which operates at 4 kHz and supports a frame rate of 10 frames/s for an image of 800×800 pixels. Once relevant areas have been identified, it is possible to take high-density pixel maps of 1600×1600 pixels at a rate of 0.2 seconds per frame. However, high signal-to-noise ratio (SNR) images require averaging of several frames. We found that averaging four frames is sufficient for the fast scanning mode, which we use for fast visualization of features in the sample, while average of 8 frames is necessary for the slow scanning mode, employed for recording high SNR images. Therefore, the fast scanning mode used has a rate of 0.4 seconds per frame (average of four frames of 800×800 pixels), while the slow scanning mode has a rate of 1.6 seconds per frame (average of 8 frames of 1600×1600 pixels).

Along with the fast mechanical scanner 24, high-speed acquisition electronics 16 is needed to capture the data. We use a high speed four channel 14-bit analog-to-digital (A/D) converter to process the data. The A/D card features a sampling rate of 120 MS/s and a 1 GS memory, more than sufficient to acquire imaging data at 10 frames/s. The card is controlled through a C++ based software and a general user interface (GUI) for the final user-friendly version of scanning software (Intelligent Imaging Innovations, Denver, Colo.).

The useful aperture for the resonant scanner 24 is 12 mm×9.25 mm, while for the right hand Y mirror is 10 mm. The beam expander 32 of our system has a 1.8× magnification, which was determined by the maximum beam diameter of 9 mm allowed by the scanning mirror 24 and the objective entrance pupil diameter, 15 mm. Therefore, a FOV of 0.8×0.8 mm² would require an angle $\phi$ of 2.4° (Eq.1) at the back aperture of the objective 34 and a 4.3° scanning angle of the mirrors 24 and 26. These were the parameters used for designing the beam expander 32.

We employed a relay lens system 30 between the scanning mirrors 24 and 26 to reduce the vignetting and the beam motion at the back aperture of the objective 34 as described above. We built the relay lens system 30 and beam expander system 32 by using off-the-shelf achromat lenses as a cost-effective solution. The lenses were selected such that the root mean square (RMS) wavefront error resulted from the system was not larger than 0.07λ, a criterion associated with "diffraction-limited" performance (Marechal criterion). Simulation and optimization of both the beam expander 32 and the relay imaging systems 30 were carried out using a computer-aided design software (ZEMAX, Radiant ZEMAX LLC). We performed the optimization for a maximum scanning angle of 4.3°, a Gaussian beam diameter of 9 mm (1/e²) and a beam expander magnification of 1.8. These parameters lead to a beam diameter of 16.2 mm after the expander 32, overfilling the back aperture of the objective 34 (XLPL25XWMP, Olympus) and to a FOV of 800× 800 μm². The primary optimization wavelength was 800 nm, the wavelength of interest for our application, skin imaging. We describe below in detail the components and the overall performance of the relay lens system 30 and the beam expander 32.

In addition to beam expander 32 the beam diameter of the laser 10 may be increased by insertion of a simple beam expander at its output before optically coupling the beam to the resonant scanning mirror 24.

Relay Lens System

Figure 3A:
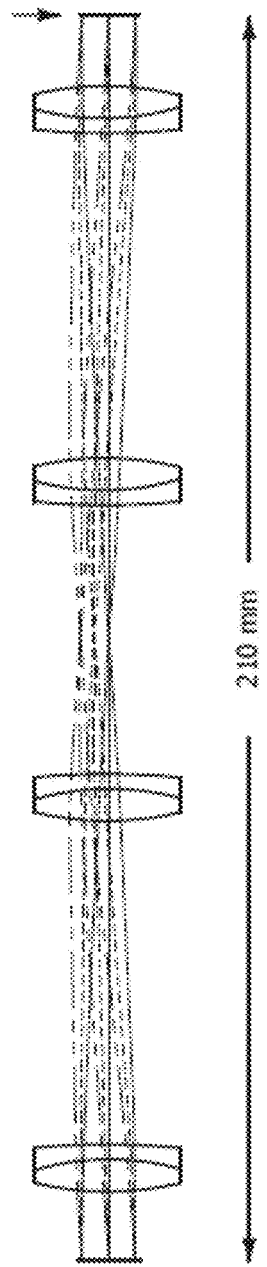
FIG. 3A is a schematic of an optical layout of the relay lens, where the arrow indicates the image surface at which the aberrations were calculated.
Figure 3B:
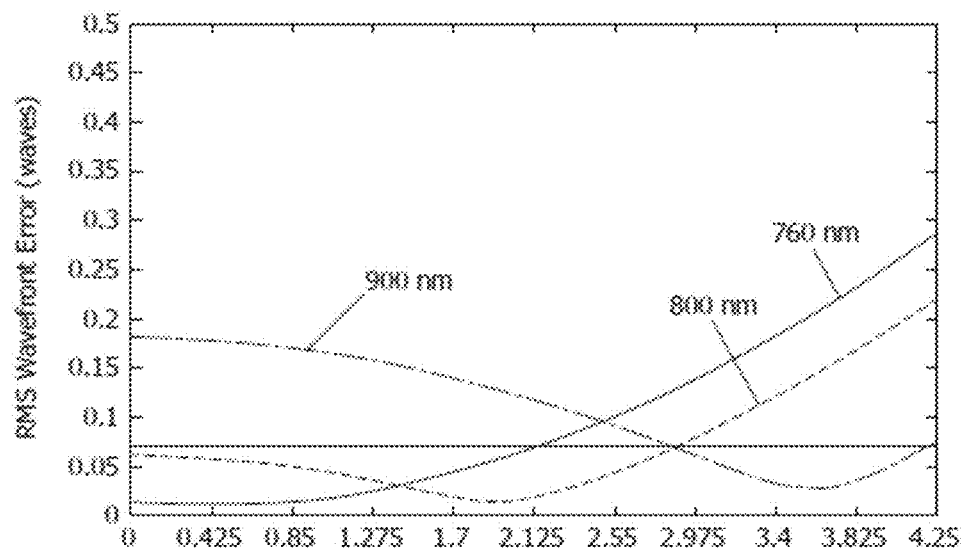
FIG. 3B is a graph of the RMS wavefront error as a function of field with respect to the diffraction limited value (horizontal line) of the relay lens.

We selected four commercially available achromat lenses to form a 1:1 relay lens imaging system 30 (026-1130, Optosigma and PAC046, Newport—2 pairs of each). The RMS wavefront error corresponding to 800 nm is 0.06. The RMS wavefront distribution with respect to the field indicates that more than ⅔ of the FOV is diffraction-limited (FIG. 3B).

Beam Expander

Figure 4B:
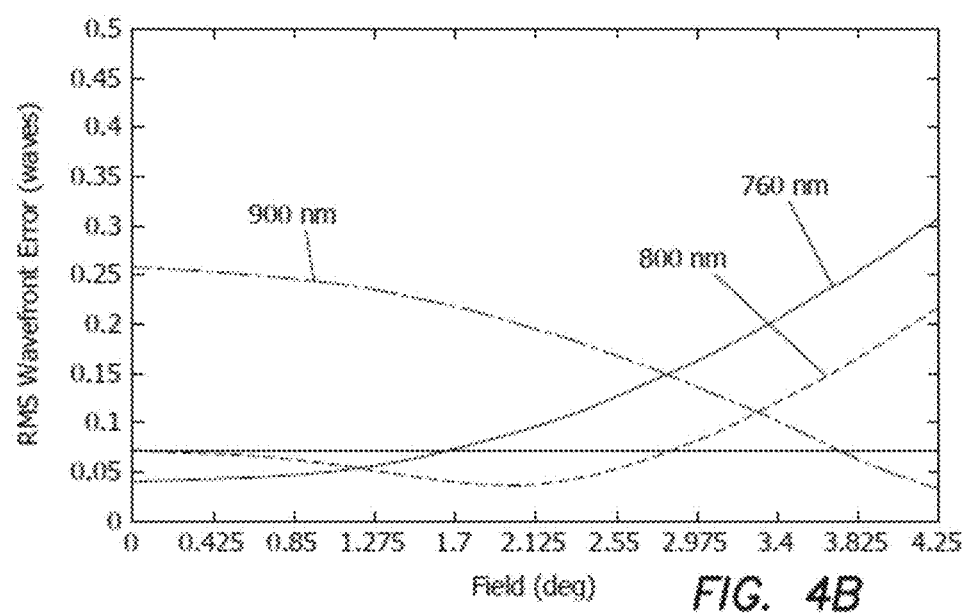
FIG. 4B is a graph of the RMS wavefront error as a function of field with respect to the diffraction limited value (horizontal line) of the beam expander.

The beam expander imaging system 32 consists of four doublet achromatic lenses (AC300-080-B Thorlabs;

PAC046, Newport; 026-1180 and 026-1220 Optosigma). The RMS wavefront error corresponding to 800 nm is 0.07. The RMS wavefront distribution with respect to the field indicates that more than ⅔ of the FOV is diffraction-limited (FIG. 4B).

MPM Imaging System Performance

We used 0.2 µm and 0.5 µm yellow-green (505/515) fluorescent beads (Molecular Probes, Eugene, Oreg.) for measuring the lateral and the axial resolution, respectively. We measured a lateral point spread function (PSF) of 0.5±0.2 µm and an axial PSF of 2.5±0.4 µm (full-width half maximum of Gaussian fit) at 800 nm excitation wavelength. Measurements included average of 5 beads.

Figure 5A:
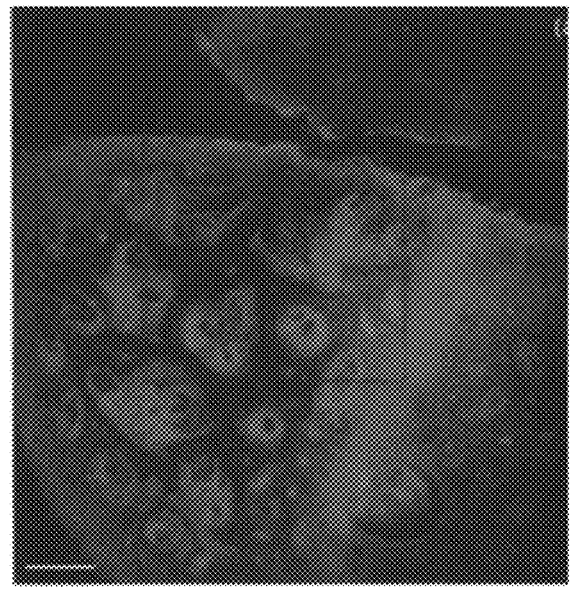
FIG. 5A is an ex vivo MPM image of human skin of a dermo-epidermal junction (DEJ) imaged with the home-built microscope by SHG (blue) and TPEF (green). TPEF signal originates from keratin in the epidermal keratinocytes and from elastin fibers (arrows) in the superficial papillary dermis, while SHG highlights the collagen fibers.
Figure 5B:
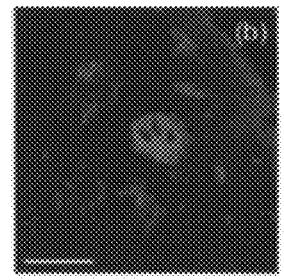
FIG. 5B is an ex vivo MPM image of human skin similar location of the DEJ in the skin sample imaged with a commercial Olympus microscope by using the same objective as in the home-built microscope. The field of view of 370×370/μm$^2$ corresponds to an area shown by the inset in FIG. 5A.
Figure 5C:
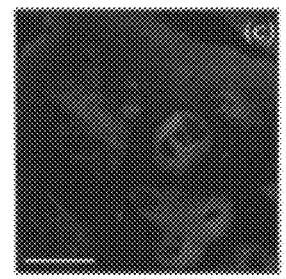
FIG. 5C is an MPM image of the DEJ acquired with the home-built microscope over an area of 370×370/μm$^2$ for comparison with the image in FIG. 5*b* acquired with the Olympus microscope. Images in FIG. 5B and FIG. 5C were acquired in similar areas with the one shown in the inset of FIG. 5A. Images were acquired at 50 μm depth in the sample. Scale bar is 100/μm.

To compare the FOVs of the home-built and of a commercial Olympus laser-scanning microscope, we imaged the same sample with each microscope using the same objective 34 (Olympus, XLPL25XWMP). For an adequate comparison of the maximum FOV covered by each microscope, the scanning was set such that the FOVs would show similar uniformity of the TPEF signal from a fluorescein sample. Therefore a FOV of 820×820 µm$^2$ for the home-built microscope corresponded to an area of 370×370 µm$^2$ scanned by using the Olympus microscope. To illustrate this comparison we used images acquired in a sample of discarded human skin tissue fixed in formalin. FIGS. 5A-5C show representative images of the dermo-epidermal junction (DEJ) of human skin acquired at 50 µm depth, at the maximum FOV with the home-built microscope (FIG. 5A) and a commercial Olympus microscope (FIG. 5B). To compare the features resolved in similar FOVs, an image of the DEJ was acquired with the home-built microscope over an area of 370×370 µm$^2$ (FIG. 5C).

The illustrated embodiments of the invention address two main technical challenges related to MPM skin imaging, namely limited field of view and slow acquisition rate of large skin areas. The MPM-based instrument proposed here is capable of imaging 0.8×0.8 mm$^2$ skin areas at sub-micron resolution and rates that range between 0.4 to 1.6 seconds per frame (when averaging four to eight frames for high signal-to-noise ratio, SNR). This represents a four-fold improvement in the FOV when compared to the images acquired with a commercial microscope using the same objective and 40× improvement in acquisition speed when compared to the available clinical MPM microscopes scanning the same FOV. Although fast scanning or wide field of view microscopes have been developed before, none of these systems was optimized for nonlinear optical microscopy in the clinic. Our design is tailored specifically to maximize FOV, image speed and signal collection from key molecular components in skin tissue. The disclosed technical advancements can significantly enhance the practical use of the nonlinear optical microscopy in clinical settings.

With current technology fast x/y scanning stages are becoming commercially available. For example, the Thor Labs (Newton, N.J.) ML S203 stage has scanning speeds of 250 mm/s over a travel of a 110 mm×75 mm scan field with an acceleration of 2000 mm/s$^b$ $^2$. The combination of a fast x/y scanning stage in the imaging head of the above embodiments allows a fast wide field of view scan of the skin at a lower resolution, which is data analyzed for smaller fields of interest. The identified fields of interest are then positioned by the stage for a submicron scan of the identified field of interest as disclosed above.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An apparatus based on laser-scanning nonlinear optical microscopy that can scan rapidly large areas while maintaining a sub-micron resolution comprising:
   one or more pulsed lasers to produce a laser excitation beam; and
   an imaging head optically coupled to the pulsed laser for scanning tissue with a predetermined size of a field of view with submicron resolution at a predetermined rate;
   where the imaging head comprises:
   a resonant scanning mirror optically coupled to the pulsed laser;
   a relay lens system optically coupled to the resonant scanning mirror;

a galvo mirror optically coupled to the relay lens system;

a beam expander optically coupled to the galvo mirror; and a microscope objective optically coupled to the beam expander, the microscope objective for scanning the tissue and returning a nonlinear optical signal from the tissue to the detectors and data acquisition system for providing an image.

2. The apparatus of claim 1 further comprising a data acquisition system associated with the imaging head to acquire and process submicron optical data in the predetermined size of field of view at the predetermined rate and to generate an image therefrom.

3. The apparatus of claim 1 where the resonant scanning mirror operates at at least a 4 kHz scan frequency while scanning the beam in the x direction and where the galvo mirror scans the beam in the y direction.

4. The apparatus of claim 1 where the resonant scanning mirror scans the beam in the x direction and the galvo mirror scans the tissue in the y direction.

5. The apparatus of claim 1 where the microscope objective provides submicron resolution by being a high numerical aperture (NA)—low magnification combination microscope objective.

6. The apparatus of claim 1 where the beam has a large diameter, where the microscope objective has a back aperture and where the relay lens system and beam expander are designed in order to compensate for the optical aberrations introduced by the large beam diameter and scanning angles and to overfill the back aperture of the microscope objective.

7. The apparatus of claim 5 where the relay lens system comprises four achromat lenses forming a 1:1 relay lens imaging system with an RMS wavefront error at 800 nm of 0.06 and more than ⅔ of the FOV being diffraction-limited.

8. The apparatus of claim 5 where the beam expander comprises four doublet achromatic lenses with an RMS wavefront error at 800 nm of 0.07 and more than ⅔ of the FOV being diffraction limited.

9. The apparatus of claim 1 where the relay lens system and beam expander each have an optical axis and where the optical axes of the relay lens system and beam expander are configured at right angles to each other as coupled through the galvo mirror.

10. The apparatus of claim 1 further comprising a folding mirror and where the relay lens system and beam expander each have an optical axis and where the optical axes of the relay lens system and beam expander are folded parallel to each other as coupled through the folding mirror and the galvo mirror to provide a compact optical layout.

11. A method for scanning tissue with a predetermined size of a field of view with submicron resolution at a predetermined rate comprising:

generating a pulsed laser beam;

scanning the pulsed laser beam with a resonant scanning mirror;

coupling the scanned pulsed laser beam from the resonant scanning mirror to a relay lens system optically coupled to the resonant scanning mirror;

scanning the pulsed laser light from the relay lens system with a galvo scanning mirror;

coupling the scanned pulsed laser beam from the galvo scanning mirror to a beam expander;

overfilling a back aperture of a microscope objective optically coupled to the beam expander; and returning a scanned nonlinear optical signal from the tissue to an image and data acquisition system.

12. The method of claim 11 further comprising generating at least two pulsed lasers beams at different frequencies, each of the two pulsed laser beams coupled to the resonant scanning mirror, to the relay lens system, to the galvo scanning mirror, to the beam expander, to the microscope objective and returned to the image and data acquisition system for separate acquisition and processing.

13. The method of claim 11 where scanning the pulsed laser beam with the resonant scanning mirror comprises scanning the pulsed laser beam with the resonant scanning mirror at at least a 4 kHz scan frequency in an x direction and steering the laser beam in an orthogonal y direction with the galvo scanning mirror.

14. The method of claim 11 further comprising providing the microscope objective with a high numerical aperture (NA)—low magnification combination to achieve the submicron resolution.

15. The method of claim 11 where generating the pulsed laser beam comprises generating a beam with a large diameter, and further comprising providing a relay lens system and beam expander arranged and configured to compensate for the optical aberrations introduced by the large beam diameter and scanning angles and to overfill the back aperture of the microscope objective.

16. The method of claim 15 where providing the relay lens system comprises providing four achromat lenses forming a 1:1 relay lens imaging system with an RMS wavefront error at 800 nm of 0.06 and more than ⅔ of the FOV being diffraction-limited.

17. The method of claim 15 where providing the beam expander comprises providing four doublet achromatic lenses with an RMS wavefront error at 800 nm of 0.07 and more than ⅔ of the FOV being diffraction limited.

18. An apparatus for performing nonlinear optical laser microscopy of tissue with submicron resolution at a predetermined clinical scanning rate comprising:

a source of pulsed laser light beam;

a resonant scanning mirror optically coupled to the source of a multiple frequency pulsed laser light beam;

a relay lens system optically coupled to the resonant scanning mirror to avoid vignetting and reduction of a field of view of the multiple frequency pulsed laser light beam when scanned;

a galvanometer scanning mirror optically coupled to the relay lens system for scanning the multiple frequency pulsed laser light beam in an x and y direction;

a beam expander optically coupled to the galvanometer scanning mirror; and a high numeric aperture, low power microscope objective optically coupled to the beam expander, the microscope objective having a back aperture which is overfilled by the beam expander to achieve submicron resolution of scanned tissue and returning a nonlinear optical signal from the scanned tissue to the image and data acquisition system, the resonant scanning mirror and galvanometer scanning mirror achieving the predetermined clinical scanning rate of the tissue.

19. The apparatus of claim 18 further comprising an image and data acquisition system to acquire and process submicron optical data in a predetermined clinical size of a field of view at the predetermined clinical scanning rate.

20. The apparatus of claim 18 where the relay lens system comprises four achromat lenses forming a 1:1 relay lens imaging system with an RMS wavefront error at 800 nm of 0.06 and more than ⅔ of the FOV being diffraction-limited.

21. The apparatus of claim 18 where the beam expander comprises four doublet achromatic lenses with an RMS wavefront error at 800 nm of 0.07 and more than ⅔ of the FOV being diffraction limited.

22. The apparatus of claim 18 further comprising a fast x/y scanning stage disposed proximate to the microscope objective for positioning the tissue relative to the microscope objective to allow for a fast wide field of view scan of the tissue at a lower resolution, which is data analyzed for smaller fields of interest, the identified fields of interest being positioned by the stage for a submicron scan of the identified field of interest.

23. The apparatus of claim 18 where the source of pulsed laser light beam, the resonant scanning mirror, the relay lens system, the galvanometer scanning mirror, the beam expander, and the high numeric aperture low power microscope objective are combined in a single imaging head as a compact integrated optical system.

24. The apparatus of claim 18 further comprising an optical arm, and where the resonant scanning mirror, the relay lens system, the galvanometer scanning mirror, the beam expander, and the high numeric aperture low power microscope objective are combined in a single imaging head, and where the source of pulsed laser light beam is exterior to the imaging head and coupled thereto by the optical arm.

* * * * *